United States Patent [19]

Mekalanos et al.

[11] Patent Number: 5,098,998
[45] Date of Patent: Mar. 24, 1992

[54] CHOLERA VACCINES AND PEPTIDES

[75] Inventors: John J. Mekalanos, Framingham, Mass.; Ronald K. Taylor, Memphis, Tenn.

[73] Assignee: President and Fellows of Harvard College, Cambridge, Mass.

[21] Appl. No.: 188,016

[22] Filed: Apr. 29, 1988

Related U.S. Application Data

[63] Continuation-in-part of Ser. No. 43,907, Apr. 29, 1987, abandoned.

[51] Int. Cl.$^5$ .................... C07K 13/00; C07K 15/00; A61K 37/02
[52] U.S. Cl. .................... 530/350; 530/825; 514/12; 424/92
[58] Field of Search .................... 530/350, 324–328; 435/71.2, 69.1; 424/88, 92; 514/12

[56] References Cited

PUBLICATIONS

Taylor, R. et al., 1986, Ann. Sclavo O(1-2):51-62, Identification of a Pilus Colonization Factors . . . , abstract only.
Yamamoto, T. et al., 1987, J. Bacteriol., 169(3): 1352-7, Evolutionary Origin . . . , 1987 abstract only.
Ehara, M. et al., Trop. Med. 28(1):21-34. 1986, Fibrige of Vitrio Cholerae 0-1 . . . , abstract only.
Taylor et al., Proc. Natl. Acad. Sci. U.S.A. 84:2833, May 1987.
Sanchez et al., FEBS Letters, "Immunoactive Chimeric ST-LT Enterotoxins of *Escherichia coli* Generated by In Vitro Gene Fusion", 208:194-198 (Nov. 1986).
Manning et al., Infection and Immunity, "Molecular Cloning and Expression in *Escherichia coli* K-12 of the O Antigens of the Inaba and Ogawa Serotypes of the Vibrio Cholerae O1 Lipopolysaccharides and Their Potential for Vaccine Development", 53:272-277 Aug. 1986.
Jacob et al., Infection and Immunity, "Immunity to Heat-Labile Enterotoxins of Porcine and Human *Escherichia coli* Strains Achieved with Synthetic Cholera Toxin Peptides", 52:562-567 (May 1986).
Black et al., Advances in Research on Cholera and Related Diarrheas, "Oral Immunization with Killed Whole Vibrio and B Subunit or Procholeragenoid Combination Cholera Vaccines: Immune Response and Protection from V. Cholerae Challenge", pp. 271-275 (1986).
Kaper et al., Vaccines, "Development and Testing of a Recombinant Live Oral Cholera Vaccine", pp. 107-111 (Jun. 1985).
Clements et al., Infection and Immunity, "Construction of a Potential Live Oral Bivalent Vaccine for Typhoid Fever and Cholera-*Escherichia coli*-Related Diarrheas", 46:564-569 (Nov. 1984).
Formal et al., Infection and Immunity, "Oral Vaccination of Monkeys with an Invasive *Escherichia coli* K-12 Hybrid Expressing Shigella flexneri 2a Somatic Antigen", 46:465-469 (Nov. 1984).
Klipstein et al., Infection and Immunity, "Properties of Cross-Linked Toxide Vaccines Made with Hyperantigenic Forms of Synthetic Escherichia coli Heat-Stable Toxin", 44:268-273 (May 1984).
Gaastra et al., Microbiological Reviews, "Host-Specific Fimbriae Adhesins of Noninvasive Enterotoxigenic *Escherichia coli* Strains", 46:129-161 (Jun. 1982).
Levine et al., Acute Enteric Infections in Children, "Volunteer Studies in Development of Vaccines Against Cholera and Enterotoxigenic *Escherichia coli*: a Review", chapter 26, pp. 443-549 (1981).
Mekalanos et al., Infection and Immunity, "Purification of Cholera Toxin and Its Subunits: New Methods of Preparation and the Use of Hypertoxinogenic Mutants", 20:552-558 (May 1978).
Mekalanos et al., Infection and Immunity, "Simple Method for Purifying Choleragenoid, the Natural Toxoid of Vibrio Cholerae", 16:789-795 (Jun. 1977).

(List continued on next page.)

Primary Examiner—Margaret Moskowitz
Assistant Examiner—T. Cunningham

[57] ABSTRACT

The gene encoding the TcpA pilus has been cloned. It encodes a protein useful in live, killed-cell, and synthetic vaccines. Protein production is enhanced by specific medium conditions.

3 Claims, 1 Drawing Sheet

```
ATG ACA TTA CTC GAA GTG ATC ATC GTT CTA GGC ATT ATG GGG GTG GTT TCG
Met Thr Leu Leu Glu Val Ile Ile Val Leu Gly Ile Met Gly Val Val Ser

GCG GGG GTT GTT ACT CTG GCG CAG CGT GCG ATT GAT TCG CAG AAT ATG ACC
Ala Gly Val Val Thr Leu Ala Gln Arg Ala Ile Asp Ser Gln Asn Met Thr

AAG GCC GCG CAA AGT CTC AAT AGT ATC GTT GCA CTG ACA CAG ACA TAC
Lys Ala Ala Gln Ser Leu Asn Ser Ile Gln Val Ala Leu Thr Gln Thr Tyr

CGT GGT CTA GGT AAT TAT CCA GCA ACA GCT GAT GCG ACA GCT GCT ATT AAG
Arg Gly Leu Gly Asn Tyr Pro Ala Thr Ala Asp Ala Thr Ala Ala Ser Lys

CTA ACT TCA GGC TTG GTT AGT TTA GGT AAA ATA TCA TCC GAT GAG GCA AAA
Leu Thr Ser Gly Leu Val Ser Leu Gly Lys Ile Ser Ser Asp Glu Ala Lys

AAC CCA TTC ATT GGT ACA AAT ATG AAT ATT TTT TCA TTT CCG CGT AAT GCA
Asn Pro Phe Ile Gly Thr Asn Met Asn Ile Phe Ser Phe Pro Arg Asn Ala

GCA GCT AAT AAA GCA TTT GCA ATT TCA GTG GAT GGT CTG ACA ACG GCT CAA
Ala Ala Asn Lys Ala Phe Ala Ile Ser Val Asp Gly Leu Thr Gln Ala Gln

TGC AAG ACA CTT ATT ACC AGT GTC GGT GAT ATG TTC CCA TAT ATT GCA ATC
Cys Lys Thr Leu Ile Thr Ser Val Gly Asp Met Phe Pro Tyr Ile Ala Ile

AAA GCT GGT GGC GCA GTA GCA CTT GCA GAT CTA GGT GAT TTT GAG AAT TCT
Lys Ala Gly Gly Ala Val Ala Leu Ala Asp Leu Gly Asp Phe Glu Asn Ser

GCA GCA GCG GCT GAG ACA GGC GTT GGT GTG ATC AAA TCT ATC GCT CCC GCT
Ala Ala Ala Ala Glu Thr Gly Val Gly Val Ile Lys Ser Ile Ala Pro Ala

AGT AAG AAT TTA GAT CTA ACG AAC ATC ACT CAC GTT GAG AAA TTA TGT AAA
Ser Lys Asn Leu Asp Leu Thr Asn Ile Thr His Val Glu Lys Leu Cys Lys

GGT ACT GCT CCA TTC GGC GTT GCA TTT GGT AAC AGC TAA
Gly Thr Ala Pro Phe Gly Val Ala Phe Gly Asn Ser
```

OTHER PUBLICATIONS

Kanoh, "Transferable R Plasmids Isolated from Vibrio Cholerae", Abstract, p. 357, 10-Microbial Biochem, vol. 95, 1981.

Mel'nikova, "Study of Natural Plasmids P and Vib of the Cholera Vibrio", Abstract, p. 151, 3-Biochem. Genetics, vol. 101, 1984.

Kanoh, "Transferable R. Plasmids Isolated from Vibrio Cholerae Eltor", Abstract, Biol. Abstr. 73(5):3266, Genetics of Bacteria and Viruses.

Holmgren et al., "Nonimmunoglobulin Fraction of Human Milk Inhibits Bacterial Adhesion (Hemagglutination) and Enterotoxin Binding of E. coli and Vibrio Ccholerae", Biol. Abstr. 73(2):1128, Medical and Clinical Microbiology.

Al-Kaissi et al., "Preparation of Properties of Vibrio Cholerae Antifimbrial Antibody", Journal of Applied Bacteriology 1985, 58:221-229.

Ehara et al., "Purification and Partial Characterization of Fimbriae of Vibrio Cholerae 01", Vaccine in Press, 1986.

Taylor et al., "Safe, Live Vibrio Cholerae Vaccines?", Vaccine, vol. 6, (1988).

Taylor et al., Chemical Abstracts, vol. 107, 1987, p. 1723.

Taylor et al., Biol. Abstr. 84(4): AB-443, Genetics of Bacteria and Viruses.

FIG. 1

```
ATG ACA TTA CTC GAA GTG ATC ATC GTT CTA GGC ATT ATG GGG GTG GTT TCG
Met Thr Leu Leu Glu Val Ile Ile Val Leu Gly Ile Met Gly Val Val Ser

GCG GGG GTT GTT ACT CTG GCG CAG CGT GCG ATT GAT TCG CAG AAT ATG ACC
Ala Gly Val Val Thr Leu Ala Gln Arg Ala Ile Asp Ser Gln Asn Met Thr

AAG GCC GCG CAA AGT CTC AAT AGT ATC CAA GTT GCA CTG ACA CAG ACA TAC
Lys Ala Ala Gln Ser Leu Asn Ser Ile Gln Val Ala Leu Thr Gln Thr Tyr

CGT GGT CTA GGT AAT TAT CCA GCA ACA GCT GAT GCG ACA GCT GCT AGT AAG
Arg Gly Leu Gly Asn Tyr Pro Ala Thr Ala Asp Ala Thr Ala Ala Ser Lys

CTA ACT TCA GGC TTG GTT AGT TTA GGT AAA ATA TCA TCC GAT GAG GCA AAA
Leu Thr Ser Gly Leu Val Ser Leu Gly Lys Ile Ser Ser Asp Glu Ala Lys

AAC CCA TTC ATT GGT ACA AAT ATG AAT ATT TTT TCA TTT CCG CGT AAT GCA
Asn Pro Phe Ile Gly Thr Asn Met Asn Ile Phe Ser Phe Pro Arg Asn Ala

GCA GCT AAT AAA GCA TTT GCA ATT TCA GTG GAT GGT CTG ACA ACG GCT CAA
Ala Ala Asn Lys Ala Phe Ala Ile Ser Val Asp Gly Leu Thr Thr Ala Gln

TGC AAG ACA CTT ATT ACC AGT GTC GGT GAT ATG TTC CCA TAT ATT GCA ATC
Cys Lys Thr Leu Ile Thr Ser Val Gly Asp Met Phe Pro Tyr Ile Ala Ile

AAA GCT GGT GGC GCA GTA GCA CTT GCA GAT CTA GGT GAT TTT GAG AAT TCT
Lys Ala Gly Gly Ala Val Ala Leu Ala Asp Leu Gly Asp Phe Glu Asn Ser

GCA GCA GCG GCT GAG ACA GGC GTT GGT GTG ATC AAA TCT ATC GCT CCC GCT
Ala Ala Ala Ala Glu Thr Gly Val Gly Val Ile Lys Ser Ile Ala Pro Ala

AGT AAG AAT TTA GAT CTA ACG AAC ATC ACT CAC GTT GAG AAA TTA TGT AAA
Ser Lys Asn Leu Asp Leu Thr Asn Ile Thr His Val Glu Lys Leu Cys Lys

GGT ACT GCT CCA TTC GGC GTT GCA TTT GGT AAC AGC TAA
Gly Thr Ala Pro Phe Gly Val Ala Phe Gly Asn Ser
```

CHOLERA VACCINES AND PEPTIDES

This application is a continuation-in-part of Mekalanos, entitled "Cholera Vaccines", U.S. Ser. No. 043,907 filed Apr. 29, 1987, (now abandoned), assigned to the same assignee as the present application and the whole specification and figure of which is hereby incorporated by reference.

BACKGROUND OF THE INVENTION

This invention relates to immunological protection against *Vibrio cholerae*.

*V. cholerae* is a bacterial species that can cause a diarrheal disease in humans by colonizing in the small intestine and secreting a protein toxin. The action of the cholera toxin has been well characterized. The toxin includes two subunits, the A and B subunits; the B subunit has no known toxic activity but provides a degree of immunological protection when used as a component of a vaccine. Black et al. 1986 *In Advances in Research on Cholera and Related Diarrheas* 3:271. eds. Kuwahara et al.

In addition to B sub-unit vaccines, vaccines for cholera also include denatured whole cholera toxin, killed whole cells of *V. cholerae* grown usually on a solid medium at pH 7.5–8.0, and mixtures of killed cells and inactivated toxin molecules. Other vaccines include live attenuated *V. cholerae* strains which do not produce the A subunit of cholera toxin, and attenuated strains of heterologous non-*Vibrio cholerae* carriers, that is, non-*V. cholerae* strains, e.g., *Salmonella typhi* Ty21A having cloned genes encoding the cholera protective 01 antigen (J. Infectious Desease 131:553–558, 1975).

Ehara et al. (Trop. Med. 28:21, 1986; and Vaccine, 1988) describe purification of fimbriae of *V. cholerae* having a structural subunit protein of about 16 kD. This protein is not stained by Coomassie blue and its haemagglutination (HA) titre is mannose sensitive. AL-Kaissi et al. (J. App. Bact. 58:221, 1985) also describe fimbriae which have a mannose sensitive HA titre.

Kanoh (Nippon Saikingaku Zasshi, 36:465, 1981), Melnikova et al. (Mol. Biol. Genet. Russian 2:18, 1982), and Kanoh (Jpn. J Bacteriol. 36:465, 1981) describe sex pili of *V. cholerae*, encoded by plasmid genes. Holmgren et al (Infect. Immun. 33:136, 1981) describe various *E. coli* fimbriae.

SUMMARY OF THE INVENTION

This invention provides a *V. cholerae* surface protein structure called a pilus, specifically a toxin coregulated pilus ("TcpA pilus") that is instrumental for adherence of *V. cholerae* to the intestine and for colonization in the intestine. Production of this pilus is significantly enhanced under certain laboratory culture conditions, and thus the invention also provides a method for cultivation of *V. cholerae* to produce the TcpA pilus. Further, the invention features a method for production of the B subunit of cholera toxin, which is co-regulated with production of TcpA pilus and is also useful as a vaccine component In addition, we have cloned the structural gene for the TcpA pilus subunit and determined the inferred amino acid sequence of the TcpA protein. The use of these materials and information enables production of several different types of cholera vaccines that are able to stimulate production of protective antibodies that recognize the TcpA pilus and thus inhibit adherence to, and colonization of, the human intestine by *V. cholerae.*

In a first aspect, the invention features: 1) a purified polypeptide comprising at least one immunogenic determinant of (or a polypeptide cross-reactive with) the TcpA pilus of *V. cholerae,* preferably the whole of the TcpA pilus; 2) an oligonucleotide encoding at least five contiguous amino acids of the TcpA pilus of *V. cholerae* and the polypeptide encoded by that oligonucleotide; and 3) an oligonucleotide, comprising 15 base pairs, having substantially the nucleic acid sequence of apart of a gene encoding the TcpA pilus of *V. cholerae.*

By purified is meant that the TcpA pilus, or polypeptide forming a part of the pilus, is separated from one or more components with which it naturally occurs, for example OmpU outer membrane protein. Preferably, the polypeptide is provided essentially free of these naturally occuring components, represents greater than 50% of total protein in a preparation, and has less than 50% of the normal OmpU protein level.

By polypeptide is meant a sequence of amino acids encoding apart of TcpA which is antigenetically active, and thus induces antibody formation, the antibodies of which recognize naturally occuring TcpA.

In a second aspect, the invention features a method for producing a vaccine, comprising growing a culture of *V. cholerae* cells in growth medium under conditions in which TcpA is produced t higher levels than normal, preferably in a medium having a pH of about 6.5, or less, or using cells having mutated htx gene; preferably, the vaccine is a whole cell vaccine and the method further comprises killing the cells; or the vaccine comprises a TcpA pilus, and the method further comprises harvesting the *V. cholerae* and purifying the TcpA pilus from the cells; or the vaccine comprises B subunit of cholera toxin and the method further comprises harvesting the *V. cholerae* cells and purifying the B subunit of cholera toxin from the cells.

In other aspects, the invention features a vaccine comprising TcpA pilus, or an immunogenic determinant thereof, preferably purified as described above; a heterologous (non-*V. cholerae*) bacterial strain comprising nucleic acid encoding an immunogenic fragment of TcpA pilus; a hybrid polypeptide comprising an immunogenic determinant of TcpA pilus of *V. cholerae* and an immunogenic determinant of the B subunit of protein, and the nucleic acid encoding therefor. The invention also features a bacterial cell having at least 1% total protein as TcpA. Preferably the cell lacks toxic levels of cholera toxin; and most preferably the cell is a *Vibrio cholerae* having a mutated htx gene.

DESCRIPTION OF THE PREFERRED EMBODIMENTS

Structure

TcpA pilus

The FIGURE shows the DNA sequence, and corresponding amino acid sequence, of the gene encoding TcpA pilus in *V. cholerae.*

The TcpA pilus is an example of a filamentous surface component (pilus) of *V. cholerae* cells. When isolated from whole cells of *V. cholerae* 0395 it has an apparent molecular weight in SDS polyacryamide gel electrophoresis of 20.5 KD. The TcpA pilus is associated with the macromolecular filamentous structures on the surface of *V. cholerae* and can be partially purified by differential centrifugation. The pilus is produced in significant quantities only under certain environmental conditions of growth of *V. cholerae* cells. For example, its production is best at a low pH, preferably pH 6.5 or less, and is virtually undetectable at a pH above 7.5. Further, its production is best at a low ionic strength equivalent to between 50–100 mM NaCl. Other factors controlling TcpA pilus production include the presence of amino acids in the growth medium (e.g. LB, see below), aeration (e.g., 0.5–2 liter/min per 6 liter of medium), the type of medium (preferably liquid), and incubation temperature (preferably 25°–30° C.). In addition, the TcpA pilus is only produced at a particular stage of growth of the *V. cholerae* cells (e.g., stationary phase). These growth conditions generally are not optimal for cellular growth; rather they are optimal for production of TcpA pilus.

TcpA pili form bundles of filaments when purified, the protein is stained by Coomassie blue, and its haemagglutination activity is not affected by mannose.

To measure the percentage of TcpA in a preparation, a portion of the preparation is run in a gel, reacted with antibody to TcpA to locate the protein band corresponding to TcpA, the band is cut from a gel, and the amount of TcpA is determined. Total protein is determined by standard procedure, and used to calculate % TcpA.

The gene encoding TcpA pilus in *V. cholerae* has been cloned, as described below; its DNA sequence is shown in FIG. 1. The TcpA gene is chromosomally located. Using this cloned DNA, related DNA from other strains of *V. cholerae*, or synthetic DNA encoding substantially the same amino acid sequence shown in the figure, the TcpA pilus can be produced in other bacterial strains, using standard procedures. Thus, the term TcpA pilus includes proteins having amino acid modifications which do not substantially affect the antigenicity of the molecule. Similarly the gene encoding TcpA includes genes encoding for such amino acid modifications, or for antigenic portions of TcpA. For example, the DNA can be introduced into any standard vector and transformed into bacterial strains capable of expressing the TcpA pilus; an example of this is given below.

EXAMPLE 1

Cloning the TcpA gene

TnphoA is a derivative of the transposon Tn5 that retains its broad host range and random insertion properties but in addition can create fusions between target genes and phoA, the alkaline phosphatase gene of *Escherichia coli* (Manoil et al. 82 *Proc. Nat'l Acad. Sci* USA 8129, 1986). Such gene fusions encode hybrid proteins composed of a carboxy terminal portion of alkaline phosphatase (PhoA) fused in frame to an amino terminal portion of a target gene product. These hybrid proteins exhibit little or no PhoA activity unless the target gene encodes a secreted or membrane spanning protein. These active fusions are easily identified as blue colonies by incorporating the chromogenic alkaline phosphatase substrate 5-bromo-4-chloro-3-indolyl phosphate (XP) into agar medium on which the bacterial cells carrying inserts of TnphoA have been plated. Because virtually all bacterial proteins implicated as virulence factors are periplasmic, extracellular, or cell surface associated, this method provides a strong enrichment for insertion mutations that may affect pathogenic properties of bacteria, such as colonization or toxin production.

Random insertions of TnphoA into the chromosome of *V. cholerae* was accomplished through the use of pRT291 a derivative of the broad host range P-group plasmid pRK290 (Mekalanos, *Nature* 276:633, 1978) that carries a copy of TnphoA (constructed by spontaneous transposition with TnphoA). Briefly, chromosomal inserts of TnphoA were obtained in *V. cholerae* strains carrying pRT291 by superinfection with the incompatible plasmid pPhlJI (Id.) and selection for resistance to kanamycin and gentamycin. *V. cholerae* colonies carrying inserts of TnphoA were screened for the PhoA+ phenotype on LB agar containing 0.2% glucose and 20 mg/ml of XP at 30° C.

A pool of several thousand *V. cholerae* colonies carrying inserts of TnphoA was screened for mutations that encoded PhoA+ fusion proteins. About 1% of the colonies carrying inserts of TnphoA were blue on this medium indicating that they carry copies of TnphoA fused to genes encoding secreted or membrane proteins that express in this medium.

Forty of these blue colonies were purified and analyzed for their total protein profile by polyacrylamide gel electrophoresis (PAGE). *V. cholerae* wild-type and mutant strains were grown in LB broth, pH 6.5 at 30° C. for 18 h with aeration. Cells were collected by centrifugation, lysed in sample buffer with a reducing agent, and analyzed by electrophoresis through a 12.5% polyacryamide slab gel in the presence of $NaDodSO_4$, as previously described by Mekalanos et al. (16 *Infect. Immun* 787, 1977).

Seven mutants have detectable differences in their protein profile showing the loss of one or more bands. One type of mutant, represented by strain RT110.21, has lost a single protein of molecular weight 20.5 KD.

A mutant lacking the 20.5 KD protein was tested for colonization defects by a competition assay involving coinfection of the mutant with the parental strain into 3–9 day old CD 1 mice essentially as described by Freter et al. 34 *Infect. Inmun.* 234, 1981. The mutant strain RT110.21, which had lost the 20.5 KD protein, showed a marked decrease in its ability to compete with the parental strain in vivo, but not in vitro. Other competition experiments performed with another independently isolated mutant lacking the 20.5 KD protein confirmed that this class of mutant is severely defective in colonization in both infant mice as well as adult rabbits.

Cell fractionation showed that the 20.5 KD protein is associated with macromolecular structures that are located on the bacterial cell surface. A nonflagellated mutant (mot-39; Mekalanos, 306 *Nature* 551, 1983) derived from strain 0395-N1 was used to partially purify these structures from sheared cells by several rounds of differential sedimentation. The strain was grown in LB broth, pH 6.5. A volume of 400 ml of broth per 2 liter flask was used and the culture was incubated at 150 revolutions per min for 16 h at 30° C. The cells were collected by centrifugation and resuspended in a buffer containing 12.5 mM tris-HCl pH 7.0, 25 mM NaCl, 4 mM $MgCl_2$, and 4 mM $CaCl_2$. After shearing the bacterial cells by passage through a 21 gauge needle, the pili were purified by several rounds of differential centrifugation to remove cells and soluble proteins. Typically, sheared cells are centrifuged at 3000×G for 20 minutes. Supernatant fluid is collected and the pellet discarded. The supernatant fluid is than centrifuged at 15,000×G for 40 minutes. The supernatant from this step is discarded and the pellet collected and resuspended in (TCP buffer). These two steps of differential centrifugation are repeated twice again. The final pellet represents purified TcpA (i.e., TcpA protein represents greater than 50% of the total cell protein) in such as preparation. The isolation of the pili was monitored by following the purification of the 20.5 kilodalton pilus subunit by PAGE. Purified pili were observed under the electron microscope after staining preparations with 2% ammonium molybdate. Examination of these preparations in the electron microscope showed long laterally associated fimbria or pili (7 nm in diameter). Individual pilus filaments could be seen on the surface of cells of strain 0395 but were not seen on cells of TnphoA induced mutants that had lost the 20.5 KD protein.

The 20 5 KD protein was further purified by electroelution after PAGE and subjected to N-terminal amino acid sequence analysis. The sequence data corresponds to that shown in the FIGURE. This sequence is highly hydrophobic and may represent part or all of a secretory signal sequence. Consistent with this conclusion, subcloning of the TnphoA fusion from strain RT110.21 and DNA sequencing has shown that the phoA gene is fused to the pilus coding sequence 92 codons downstream from the sequence encoding this hydrophobic stretch of amino acids. Two other mutants which have lost the 20.5 KD protein also have TnphoA inserts that have fused phoA to this same open reading frame, confirming that this sequence does indeed represent the structural gene for the *V. cholerae* pilus.

We have cloned the gene for the tcpA gene in two steps. First, the tcpA-TnphoA gene fusion carried by RT110.21 was cloned onto a plasmid by selecting for its kanamycin resistant phenotype in *E. coli*. A gene probe derived from the DNA sequences adjacent to this TnphoA fusion was then used to identify a cosmid clone carrying the wild type tcpA gene of strain 0395 (Id.). This plasmid, called pCS12G7, carries an active tcpA gene as shown by the following experiments:

a. When pCS12G7 is introduced into the tcpA mutant strain RT110.21, it complements its pilus defect and the plasmid carrying strain once again produces the TcpA pilus.

b. DNA sequencing of the entire tcpA gene confirmed its location on pCS12G7. This sequence is presented in the FIGURE.

c. When introduced into *V. cholerae* strains 0359-N1 or 569B-N1, pCS12G7 induces a hyper-piliation phenotype in which these strains produce 2–3 times more TcpA pili than usually produced in expression media. 569B-N1 is an Inaba serotype strain of *V. cholerae.* It carries a deletion in the ctxA gene but is ctxB+. The strain was constructed by transduction of the ctxAB $Km^r$ mutation of 0395-NT into a spontaneously highly motile derivative of 569B (strain 569B is usually nonmotile). The transductant (strain 569B-NT) was then converted to 569B-N1 by recombination with pJM290.2 (Id.)

d. When introduced into *E. coli* or *Salmonella typhimuruim* LB5000, pCS12G7 produces a protein subunit that is identical in size and immunological properties to the TcpA protein by Western blot analysis.

B. subunit of cholera toxin

The B subunit is present in cholera toxin at a ratio of 5:1 with A subunit. It has no known toxic activity and is useful as a component for vaccines against cholera. Strains of *V. cholerae* having mutations which inactivate the A subunit are known. The level of both A and B subunits can be markedly increased by growing *V. cholerae* cells in medium suitable for production of the TcpA pilus, as described above. By using mutants having inactive A subunit e.g., ctxA deletion strains (Id.), it is possible to grow cells to produce large amounts of both the B subunit and TcpA pilus simultaneously.

The reason for enhanced production of B subunit and TcpA pilus appears to be that the genes encoding these proteins are regulated by the same gene--toxR--the regulation or activity of which in turn is affected by growth conditions.

Furthermore, by using a tcpA-specific hybridization probe (a DNA fragment containing only nucleotides known to encode amino acids of the TcpA protein), we have shown that the tcpA gene is present in all strains of *V. cholerae* isolated from patients with cholera. In contrast, several environmental strains of *V. cholerae* (i.e., strains isolated from water sources, rather than patients), do not contain the tcpA gene. These observations support the contention that tcpA encodes the colonization factor for all *V. cholerae* strains implicated in human diarrheal disease. In addition, environmental strains of *V. cholerae* which do not contain the tcpA gene are known to colonize human volunteers poorly and induce little if any immunity in those volunteers. Levine et al., *In Acute Enteric Infections in Children,* Ch. 26., 1981 Elsevier. The explantation for this is that those strains cannot make the TcpA pilus and therefore cannot colonize humans or induce protective antibodies that react with the TcpA pilus.

Cholera Vaccines

The ability to produce both TcpA pilus and large amounts of B subunit make possible the construction of a variety of cholera vaccines.

a. Killed whole cell vaccine

For this vaccine *V. cholerae* cells are grown under conditions that allow high expression of the TcpA pilus and/or the B subunit of cholera toxin. We have established such conditions for strains 0395-NI, 569B-NI, and their derivatives (see Example 2 below) but have shown that these conditions can be similarly established for theoretically any strain of *V. cholerae* provided TcpA and cholera toxin B subunit production are used to optimize growth parameters. Similarly, mutant strains of *V. cholerae* can be isolated that produce TcpA and B subunit under growth conditions different from those presented here (see strain 569B htx-5 in example 2 below). The essential aspect of our invention is that cultivation of *V. cholerae* under certain growth conditions can produce cells that express TcpA pili on their surface at high level (i.e., greater than 1% of total cell protein) and thus form a suitable cholera vaccine. Once appropriate strains are grown under appropriate conditions, the cells are then killed by standard procedures, such as by treatment with glutaraldehyde or formalin. These treatments must be such as to preserve the antigenic properties of the TcpA pilus and B subunit.

This vaccine can be supplemented with purified B subunit produced by standard procedure, or by growing cells under conditions which enhance its production, and then purifying the protein by standard procedure.

EXAMPLE 2

This example demonstrates the production of cholera B subunit and piliated *V. cholerae* cells for use in killed whole cell vaccine or for preparation of purified TcpA pilus.

At least three different strains of *V. cholerae* can be used for production of piliated cells and the B subunit of cholera toxin. Strains 0395-N1 and its hyperpiliated derivative 0395-N1 (pCS12G7) are Ogawa in serotype while strains 569B N1 and its hyperpiliated, hypertoxigenic derivative 569B-N1 htx-5 are Inaba in serotype. Strain 569B-N1 htx-5 is a derivative of strain 569B-N1 carrying a htx mutation isolated by standard methods (Mekalanos, Proc. Natl. Acad. Sci. USA 75:941). We have found that in addition to causing hyperproduction of cholera toxin, the htx mutation also causes hyperproduction of the TcpA pilus under both the growth conditions outlined below as well as other growth conditions that are not usually permissive for TcpA production (e.g., high pH's such as 7.5). A cholera killed whole cell vaccine should preferably contain cells of both the Ogawa and Inaba serotypes and therefore separate cultures of one Ogawa and one Inaba strain are normally prepared. The hyperpiliated derivatives produce 2–3 times as much TcpA pilus as their parental derivatives because they either carry the high copy number plasmid pCS12G7 that contains the tcpA gene of strain 0395 (i.e, 0395-N1 pC512G7) or they carry the htx mutation (i.e., 569B-N1 htx-5). All strains are cultured as described below except that ampicillin is added to the medium to a final concentration of 50 micrograms per ml for strain 0395-N1 (pCS12G7).

Starter cultures of the selected *V. cholerae* strain are prepared in test tubes containing 2 ml of LB-6.5 medium (10 g Tryptone, 5 g yeast extract, 5 g sodium chloride, pH adjusted to 6.5 before autoclaving) and incubated at 30° C. on a roller incubator at a speed of 30 RPM of 18 h. Starting cell density of the starter culture is low (about $10^7$ per ml inoculated from a fresh agar plate culture) and after growth, autoagglutination of the bacterial cells is apparent as clumps of material easily visible to the naked eye. The bacterial cells that are clumped are allowed to settle out of the upright stationary tube and then collected from the bottom with a pipet. The clumped cells are used to inoculate 6 liters of LB-6.5 contained an appropriately designed fermentation vessel that allows air to be pumped through the medium and dispersed as fine bubbles. The culture is incubated with moderate aeration (0.5–1 liter/min) at 25° C. for 24 h during which time the culture reaches stationary phase and becomes nearly completely autoagglutinated. The clumped bacterial cells carrying TcpA pili on their surface are collected by centrifugation and resuspended in 600 ml of 0.85% sodium chloride, 10mM sodium phosphate buffer pH 7.0.

These piliated *V. cholerae* cells are then used for preparation of purified TcpA pili or killed whole cells while the cell free culture supernatant fluid is used to purify the B subunit of cholera toxin by standard methods (Mekalanos et al., *Infection and Immunity* 16:789, 1977 and 20:552, 1978).

It is anticipated that the method used to kill and preserve these piliated cells for use in the whole cell vaccine should not destroy the immunogenicity of the TcpA pili. In this regard, treatment of the piliated cells for 24–48 h with 1% glutaraldehyde or 1% formalin effectively kills the organism while maintaining the immunogenicity of the TcpA pilus. The formulation of one oral or parenteral dose of this killed whole cell vaccine should preferably include at least $10^{10}$ killed piliated *V. cholerae* cells of the Ogawa serotype (0395-N1 or 0395-N1 (pCS12G7)) and at least $10^{10}$ killed piliated *V. cholerae* cells of the Inaba serotype (569B-N1 or 569B-N1 htx-5).

The protective efficacy of such a vaccine can be further improved by including 200–500 micrograms of the purified B subunit of cholera toxin prepared from the same cultures used to prepare the piliated *V. cholerae* cells. Note that all four production strains are deleted for the A subunit of the toxin and that the above culture conditions are optimal for expression of both the TcpA pilus and the B subunit—these are the preferred types of production strains and conditions.

Alternatively, the piliated cells above could be sheared and the TcpA pilus purified by differential sedimentation, or other methods, and then used either alone or combined with the purified cholera B subunit as a vaccine.

b. TcpA pilus vaccine

This vaccine is composed of at least an immunogenic fragment of TcpA pilus (e.g., a fragment having at least one TcpA pilus determinant and preferably at least two or three such determinants). The pilus can be prepared either synthetically or from whole cells grown under appropriate conditions and then purified by standard procedure, or it can be prepared by using recombinant DNA methology. For example, a synthetic polypeptide corresponding to a fragment of the TcpA pilus amino acid sequence can be prepared by standard procedures, or a nucleic acid sequence encoding such a fragment may be expressed in an expression system, and the resulting polypeptide purified. Standard procedures can be used to identify such fragments, for example, partial deletions of the tcpA gene can be constructed, expressed as described above, and the efficacy of this partial TcpA product studied. Those fragments that have immunogenicity similar to the native TcpA pilus would be useful in such a vaccine. Similarly, polypeptides which are cross-reactive with the TcpA pilus are suitable in this invention. (By cross-reactive is meant those polypeptides which are immunoprecipitable with antibodies produced to TcpA pilus.) See generally, J. Mol. Immunol. 19:1541–1549, 1982; and J. Mol. Immunol. 21:785–793, 1984.

This vaccine may be supplemented with killed whole cells of *V. cholerae*, with B subunit, or may be used to supplement existing vaccines.

Synthetic peptides also offer an inexpensive means for producing a pure immunogen for use in vaccines. The deduced amino acid sequence of the TcpA pilin (derived from its DNA sequence) provides the essential information needed to design a synthetic peptide that might serve as an immunogen for raising antibodies that react with the TcpA pilus and block its function (cell binding). Such immunogenic peptides can be identified by a systematic approach in which non-overlapping or partially overlapping peptides are synthesized and then antibodies are raised to each. The peptides that induce antibodies which either react with and inhibit binding of the TcpA pili to host cells, or actually protect animals from virulent *V. cholerae* are then identified. These peptides carry the protective epitopes of the TcpA pilus and can therefore be used as a cholera vaccine, preferably after chemically crosslinking them to an appropriate immunologic carrier protein. The carrier protein enhances the immunogenicity of the peptide by providing "T-cell help functions." Many different proteins have been used as peptide carriers but one of the best is cholera B subunit, or the B subunit of the heat-labile enterotoxin of E. coli (Infection & Immunity 44:268–273, 1984).

EXAMPLE 3

TcpA-related Chimeric Protein Vaccine

In the same way that a chemically crosslinked TcpA-related peptide carrier protein conjugate can be used as an immunogen, genetically derived fusion proteins can also serve as immunogens in a cholera vaccine. These gene fusions are made from the structural gene for the TcpA pilus or from a synthetic DNA oligonucleotide that encodes peptide sequences related to the TcpA protein, and the gene for the carrier protein. We have made such a gene fusion between the tcpA gene and the gene for alkaline phosphatase (phoA) of E. coli and, as described above, have demonstrated the production of a fusion protein in both V. cholerae and E. coli. These fusion proteins react with antibody raised against TcpA pili and therefore would probably stimulate antibodies against the TcpA pilus if the fusion proteins were used as immunogens. This genetic approach can also be utilized to make other fusion proteins between tcpA-related DNA sequences and genes for carrier proteins like LT-B subunit cholera toxin B subunit, diptheria toxin, and tetanus toxin (FEBS Letters 208:194–198 (1986)).

c. Heterlogous live vaccines

Living cells of Salmonella, E. coli or vaccinia virus, which have been modified to be relatively non-pathogenic are transformed, or otherwise modified by recombinant DNA methodology, to encode TcpA pilus protein and preferably also the B subunit of cholera toxin. These cells or particles may be used to inoculate against cholera if they can stimulate antibody production against TcpA pilus and preferably also B subunit. Only an immunologically active fragment of either protein need be encoded by these organisms, and this vaccine can be used in conjunction with the above vaccines, or with prior vaccines.

EXAMPLE 4

This example describes the construction of a live heterologous carrier vaccine expressing the TcpA pilus subunit. Several organisms including S. typhi Ty21A (J. Infect. Dis. 131:553, 1975; Inf. & Immunity 46:564–569, 1984), other Salmonella species (Nature 291:238–239, 1981), E. coli-Shigella hybrids (Inf. & Immunity 46:465–469, 1984), and vaccinia virus (Nature 311:67, 1984; Proc. Natl. Acad. Sci. USA 80:7155, 1983), are potential live carrier vaccines that will not only immunize against homologous diseases (typhoid fever, shigellosis, small pox, etc.) but also against other diseases carried by the live carrier strain and expressed by genes for the appropriate protective immunogens. Both E. coli and S. typhimurium strains carrying the plasmid pCS12G7 or related plasmids, such as pCS12G10, produce a protein that is immunologically identical to the TcpA pilin. Thus, this plasmid or derivatives of this plasmid will provide the necessary genetic information for live carrier vaccine strains to express TcpA-related immunogens.

The method for preparation of this vaccine depends on the organism used as the live carrier vaccine strain. For bacterial carriers, plasmids expressing the TcpA pilin are introduced by transformation or conjugation, using standard procedure. Such plasmids can be integrated into the chromosome of the carrier strain to provide more stable genetic inheritance of the TcpA pilin gene. For viral carriers, the tcpA gene sequence is genetically engineered to express in host (animal or human) cells that are infected with the recombinant virus.

The efficacy of a live heterologous carrier vaccine expressing the TcpA pilin will be improved if it also expresses the B subunit of cholera toxin The introduction of the ctxB gene as well as the tcpA gene into the same strain of carrier organism is therefore preferred.

Once constructed, a live heterologous vaccine strain is compounded into a vaccine by standard procedures and administered orally or parenterally in a dose that is large enough to allow the organisms to multiply, but not cause overt disease in the vaccinated host. (e.g. about $10^6$–$10^{10}$ cells or virus particles per dose) Use The use of the above vaccines includes their inoculation into humans or other animals to prevent cholera and related infections. The vaccines can be administered using standard procedure, preferably by oral route, but also by injection. Dosages will vary from about $10^9$–$10^{10}$ live bacteria or $10^{10}$ killed bacteria, and from 10–1000 mg TcpA pilus or B subunit per kg animal body weight.

Deposits

The following deposits were made on Apr. 29, 1987, with the American Type Culture Collection (ATCC), where the deposits were given the following accession numbers:

| Deposit | Accession No |
|---|---|
| V. cholerae 0395-N1 (pCS12G7) | 67396 |
| V. cholerae 569B-N1 htx-5 | 53613 |
| S. typhimurium LB5000 (pCS12G10) | 67397 |

Applicants' assignee, President and fellows of Harvard College, represents that the ATCC is a depository affording permanence of the deposit and ready accessibility thereto by the public if a patent is granted. All restrictions on the availability to the public of the material so deposited will be irrevocably removed upon the granting of a patent. The material will be available during the pendency of the patent application to one determined by the Commissioner to be entitled thereto under 37 CFR 1 14 and 35 USC 122. The deposited material will be maintained with all the care necessary to keep it viable and uncontaminated for a period of at least five years after the most recent request for the furnishing of a sample of the deposited microorganism, and in any case, for a period of at least thirty (30) years after the date of deposit or for the enforceable life of the patent, whichever period is longer. Applicants' assignee acknowledges its duty to replace the deposit should the depository be unable to furnish a sample when requested due to the condition of the deposit.

Other embodiments are within the following claims.

We claim:

1. A purified polypeptide comprising an immunogenic determinant of the TcpA pilus of V. cholerae.

2. The polypeptide of claim 1 comprising at least eight contiguous amino acids of the amino acid sequence shown in FIG. 1.

3. The polypeptide of claim 1 comprising a TcpA pilus monomer of V. cholerae.

* * * * *